(12) United States Patent
Dubach

(10) Patent No.: US 8,887,716 B2
(45) Date of Patent: Nov. 18, 2014

(54) SUPRAGLOTTIC TUBE FOR INSERTING A LARYNX MASK

(75) Inventor: Werner F. Dubach, Maur (CH)

(73) Assignee: Deltona Innovations AG, Maur (CH)

( * ) Notice: Subject to any disclaimer, the term of this patent is extended or adjusted under 35 U.S.C. 154(b) by 284 days.

(21) Appl. No.: 13/130,512

(22) PCT Filed: Nov. 24, 2009

(86) PCT No.: PCT/CH2009/000374
§ 371 (c)(1),
(2), (4) Date: May 20, 2011

(87) PCT Pub. No.: WO2010/060227
PCT Pub. Date: Jun. 3, 2010

(65) Prior Publication Data
US 2012/0090609 A1    Apr. 19, 2012

(30) Foreign Application Priority Data

Nov. 27, 2008 (CH) ........................... 1858/08
Nov. 18, 2009 (CH) ........................... 1773/09

(51) Int. Cl.
*A61M 16/00* (2006.01)
*A61M 37/00* (2006.01)
*A61M 16/04* (2006.01)

(52) U.S. Cl.
CPC ........... *A61M 16/04* (2013.01); *A61M 16/0409* (2014.02); *A61M 16/0415* (2014.02); *A61M 16/0418* (2014.02); *A61M 16/0431* (2014.02)
USPC ............... 128/200.26; 128/207.14; 604/95.04

(58) Field of Classification Search
CPC ..................... A61M 16/0431; A61M 16/0418; A61M 16/0415; A61M 16/0409; A61M 16/04; A61M 25/0102; A61M 25/0105; A61M 25/0144; A61M 25/0147
USPC ........... 128/200.26, 207.14–207.16; 604/268, 604/524, 528, 541, 543; 600/141–142, 146
See application file for complete search history.

(56) References Cited

U.S. PATENT DOCUMENTS 4,150,676 A * 4/1979 Jackson .................... 128/207.18
4,329,983 A   5/1982 Fletcher
(Continued)

FOREIGN PATENT DOCUMENTS

EP   1938855 A1 * 7/2008
WO   9516485 A1   6/1995

OTHER PUBLICATIONS

Deltona Innovations AG., "International Preliminary Report on Patentability," PCT International Application No. PCT/CH2009/000374 filed Nov. 24, 2009 (May 31, 2011).

*Primary Examiner* — Justine Yu
*Assistant Examiner* — Douglas Sul
(74) *Attorney, Agent, or Firm* — Janet Sleath; Speckman Law Group PLLC

(57) ABSTRACT

A supraglottic tube is provided, which despite certain softness has high compressive strength in the proximal distal direction and an adjustable radius of curvature. The supraglottic tube includes at least three lumens. A guiding lumen is located between a respiration lumen and a esophageal lumen. The lumens are separated from each other by separating walls. A guiding means, which includes a pressure element and a tractive element, is located in the guiding lumen. A tractive force can be applied to the tractive element by way of a feed connector and an adjustment unit, in which the pressure element is supported, whereby the radius of curvature of the supraglottic tube can be adjusted.

17 Claims, 5 Drawing Sheets

(56) References Cited

U.S. PATENT DOCUMENTS

| | | |
|---|---|---|
| 4,529,400 A | 7/1985 | Scholten |
| 4,911,148 A * | 3/1990 | Sosnowski et al. ............ 600/136 |
| 6,210,337 B1 | 4/2001 | Dunham |
| 6,533,783 B1 | 3/2003 | Toellner |
| 7,305,985 B2 * | 12/2007 | Brain ....................... 128/200.26 |
| 7,326,176 B2 * | 2/2008 | Machiya et al. .............. 600/142 |
| 7,506,648 B2 * | 3/2009 | Brain ....................... 128/207.15 |
| 2003/0037790 A1 | 2/2003 | Brain |
| 2005/0004515 A1 * | 1/2005 | Hart et al. .................. 604/95.04 |
| 2005/0096609 A1 * | 5/2005 | Maginot et al. ................ 604/271 |
| 2006/0032505 A1 * | 2/2006 | Alfery et al. ............ 128/207.14 |
| 2007/0017527 A1 | 1/2007 | Totz |
| 2007/0028923 A1 | 2/2007 | Souris et al. |
| 2007/0260223 A1 | 11/2007 | Scheibe et al. |
| 2008/0200761 A1 | 8/2008 | Schwartz et al. |

\* cited by examiner

SUPRAGLOTTIC TUBE FOR INSERTING A LARYNX MASK

This application is the US national phase entry of International Patent Application no. PCT/CH2009/000374, filed Nov. 24, 2009, which claims priority to Swiss patent applications no. 1858/08 filed Nov. 27, 2008 and 1773/09, filed Nov. 18, 2009.

FIELD OF THE INVENTION

The present invention relates to a supraglottic tube for inserting a larynx mask via the pharynx wherein the supraglottic tube has several lumens, of which a respiration lumen serves to supply respiration air and is used for instrumentation. At least one further lumen is present as a guide lumen, in which a guide means is positioned for changing the bending radius of the tube.

BACKGROUND

Supraglottic tubes are tubes inserted into the pharynx to keep open the airways and to ventilate a patient. A classic example is a so-called larynx mask. By means of the tube a larynx mask is introduced through the central pharynx via the epiglottis into the lower pharynx and placed behind or around the larynx. Such larynx masks are used to ventilate a patient who is anaesthetised. They allow the insertion of tubes, probes, optical instruments and other instruments into the airways. At the same time larynx masks can have an oesophageal access. This allows the introduction of probes into the oesophagus and the stomach in order to remove gastric juices and other fluids as well as air from the stomach. In anaesthetised patients emptying of the stomach is intended to prevent the stomach contents flowing back into the upper respiratory tract and being aspirated into the unprotected airways (windpipe, bronchi and lungs). A further advantage of an oesophageal access is the removal of passively or actively regurgitated stomach contents from the upper oesophagus to outside, which thereby represents limited, and thus inadequate, aspiration protection.

A large number of different larynx masks are known on the market. A typical example is set out in U.S. Pat. No. 5,878,745. This shows a gastro-laryngeal mask in which the supraglottic tube is a pipe through which several tubes can be fed. These tubes have lumens which are used for ventilation and for an oesophageal access.

The combination of a larynx mask with an oesophageal passage is becoming more and more available. U.S. Pat. No. 7,040,322 also shows such a larynx mask and the supraglottic tube here is divided by means of an intermediate wall running ventral-dorsally wherein in the larger of the two lumens produced by the division a separate tube is inserted which is used to inflate or deflate a proximal area of the larynx mask.

A larynx mask with a relatively rigid supraglottic tube can be introduced more easily, whereby the rigidity of the supraglottic tube prevents adaptation of the position of the larynx mask to the anatomical conditions. Insertion into the pharyngeal cavity by means of a relatively rigid supraglottic tube can result in injury, and positioning in the pharyngeal cavity is not always reliable.

Highly flexible larynx masks tube (PROSEAL LMA®, FLEXIBLE LMA®) allow better positioning in the larynx but are more difficult and therefore occasionally more traumatic to insert and more difficult to position in the pharynx.

In the last decade anatomically curved supraglottic tubes for inserting the larynx mask have proven themselves. They not only allow simple introduction of the larynx mask into the pharynx and good positioning, but they also exhibit better sealing. Such larynx masks with a rigid, curved tube are used particularly in emergency situations. Due to the anatomically preformed shape they can also be inserted by paramedics in emergencies.

Typical examples of such larynx masks are sold under the name LMA FASTRACH® (U.S. Pat. No. 5,896,858) and LMA CTRACH®, both by the company LMA Inc. However, because of their rigidity these bent supragottic rigid tubes cannot be left in the patient over a longer period of time and are not therefore suitable for the routine treatment of patients.

A similar design is also supplied by the company Ambu GmbHl, whereby the version is sold under the name AMBU AURA 40™. The curve angle of the supraglottic tube is however greater and wider and the tube softer in consistency. The latter allows this larynx mask to be used routinely over longer periods.

Particularly when an intervention in the neck and head area has to take place, the position of the head can vary greatly and accordingly a larynx mask with a preformed relatively rigid tube can hardly be used. However if the larynx mask is correctly positioned on the larynx fixing in such position is desirable.

To increase the sealing of the larynx mask on the larynx, the "Proseal patent" (GB 9 821 771) describes a dorsal cuff which on the highly flexible supraglottic tube pushes the larynx mask away from the posterior wall of the pharynx and onto the larynx.

Finally a larynx mask is known from US 2007/0028923 with a supraglottic tube in which a further lumen is formed in the wall of the respiration lumen for passing through a cord as simple traction means. The traction means grips the distal end of the larynx mask whereby it is also bent. Controlled and active resetting is not possible.

SUMMARY

It is therefore the aim of the present invention to create a supraglottic tube which in a relatively rigid state allows improved, simple, anatomical insertion of the larynx mask, after correct positioning then allows the supraglottic tube to become flexible and, if required, allows bending of the supraglottic tube with transmission of the bending onto the larynx mask in order, in the relevant position, to be able to exert a desired pressing force around the larynx.

This objective is achieved by a supraglottic tube for inserting a larynx mask via the epiglottis wherein the supraglottic tube has several lumens, including a respiration lumen that serves to supply respiration air and is used for instrumentation, and at least one further lumen that serves as a guide lumen in which guide means are positioned for changing the bending radius of the tube, wherein the guide means comprise a pressure element and flexible traction element. In an alternative embodiment, the supraglottic tube has several lumens, of which a respiration lumen serves to supply respiration air and is used for instrumentation, and a further lumen serves as the oesophageal access, wherein a guide lumen with insertable guiding means is positioned between the respiration lumen and the oesophageal lumen, wherein the supraglottic tube has a cross-section adapted to the pharynx and the lumens are divided by ventral-dorsally running separating walls and the separating wall between the guide lumen and respiration lumen is arranged at least approximately in the centre of the supraglottic tube. As a result of this design, it is ensured that a guide means does not deform the tube in a random direction.

BRIEF DESCRIPTION OF THE DRAWINGS

Further advantageous forms of embodiment of the supraglottic tube in accordance with the invention are described below. Their relevance and action is explained in the following description with reference to the attached drawings.

DETAILED DESCRIPTION

Figure 3:
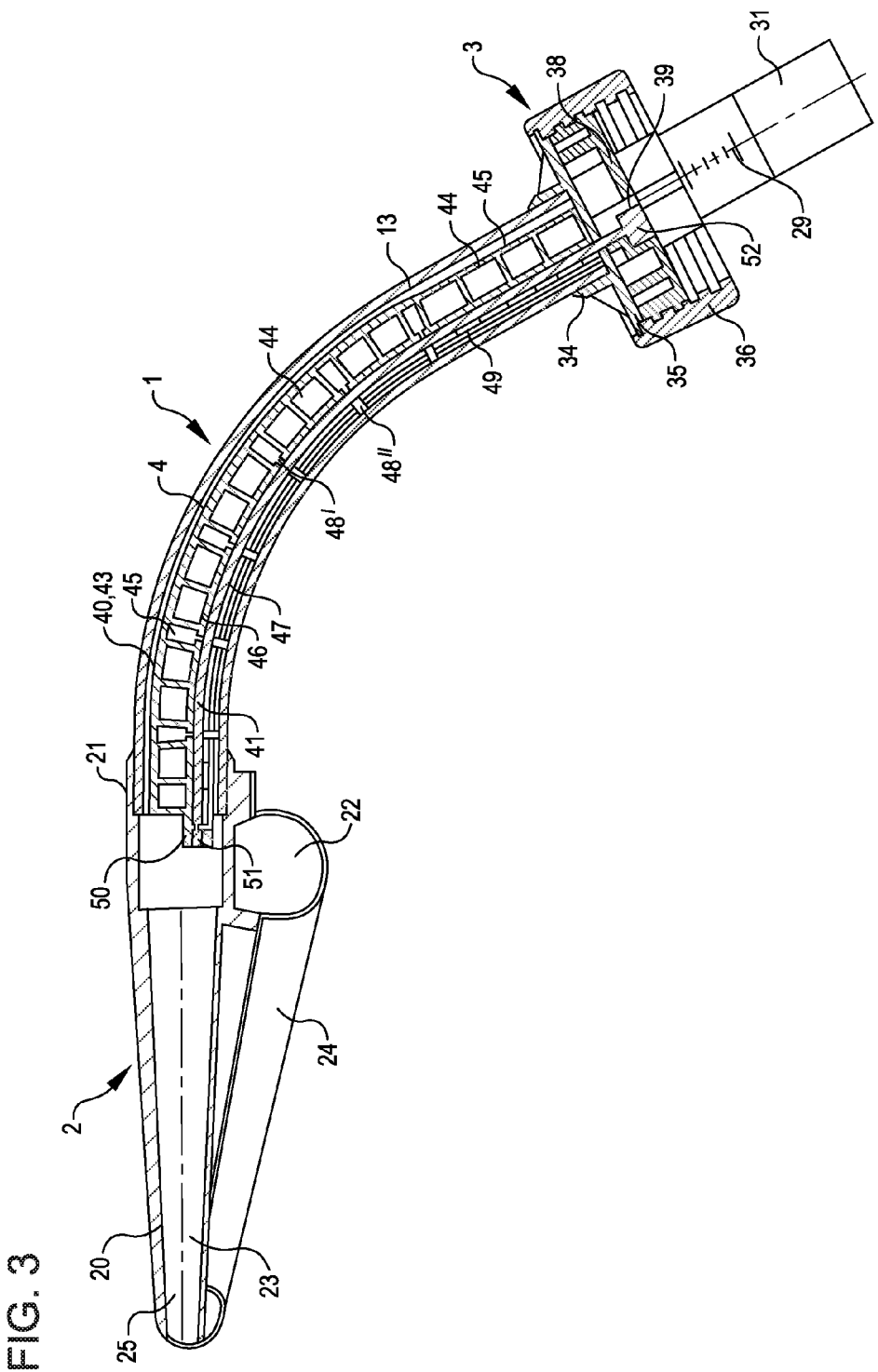
FIG. 3 shows a longitudinal section through a supraglottic tube with a distally mounted larynx mask and a proximal adjusting device.

The overall situation is shown with reference to FIG. 3. The supraglottic tube is designated with 1. At its proximal end the larynx mask 2 is attached. The distal end of the supraglottic tube is provided with a feed connector and adjusting unit 2. In relation to introduction into the patient, the side with the smaller, concave inner radius is designated as the ventral side, while the side with the outer, convex, larger radius is designated as the dorsal side. The actual larynx mask 2, which is here shown in diametric longitudinal section, has a passage section 20 which ends in a holder sleeve 21 on the distal side. In this holder sleeve 21 the proximal end of the supraglottic tube 1 is firmly held.

On the lower, ventral side of the larynx mask there is a circumferential sealing collar 22, usually known as a cuff 22. The oesophageal passage 23 passes over the cuff 22. This oesophageal passage is connected in sealed manner with a corresponding lumen of the supraglottic tube 1. The respiration air flows through laterally to the oesophageal passage and enters the inner chamber 24 which is sealed off by the cuff 22 and from which the respiration air can flow in or out of the trachea.

The actual design of the larynx mask 2 is of secondary importance for the invention. Only if a supporting element is formed on the distal end of the supraglottic tube 1 does the larynx mask 2 have to be designed so that this supporting element can be correctly held therein. This supporting element 60 essentially serves to reinforce the larynx mask in order, in particular, to prevent bending over of the tip 25 of the larynx mask during intubation. The supporting element 60 also helps to transfer the bending of the supraglottic tube to the larynx mask and prevent kinking in the area of the holder sleeve 21. The precise design of the adjusting unit and the feed connection 3 will be set out in more detail later after the description of the supraglottic tube and the guiding means.

Figure 1:
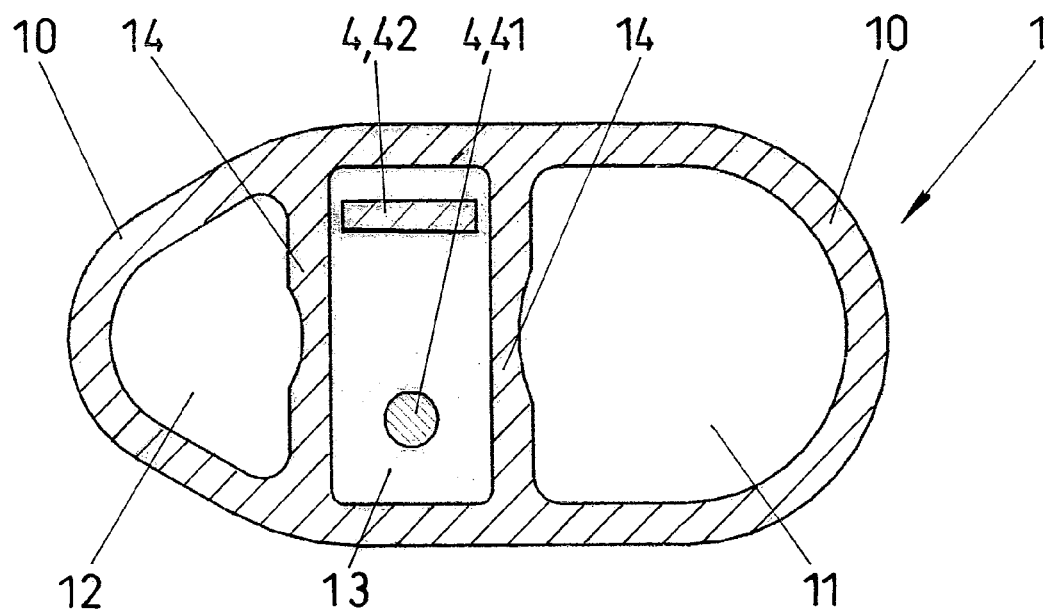
FIG. 1 shows a diametric section through the supraglottic tube in accordance with the invention with a guide means arranged in the guide lumen.

FIG. 1 shows a cross-section through the actual supraglottic tube. As usual this is made of a plastic approved for this. The supraglottic tube 1 can be produced by way of continuous extrusion or injection moulding. In the diametric cross-section in accordance with FIG. 1 the three provided lumens can be clearly seen. However it is perfectly possible that more than three lumens may be envisaged, whereby through one lumen any necessary surgical equipment, measuring probes and or an optical system, for example a fibre optic and/or an endoscope or both can be introduced.

Here too the supraglottic tube is designated with 1 overall. In the example shown here this has three different lumens. 11 is a respiration lumen for the passage of respiration air. This lumen normally has the largest cross-section. Between the respiration lumen 11 and the oesophageal lumen 12 there is a guiding lumen 13. Guiding means 4 are arranged in the guiding lumen 13. These guiding means 4 can be fixed or be interchangeable in the guiding lumen 13. This depends on whether the supraglottic tube is to be a disposable part of a sterilisable reusable part. The guiding means 4 lead to a certain reinforcement of the supraglottic tube 1 and thus to improved introduction of the larynx mask into the patient and on the other hand permit the bending radius of the supraglottic tube to be changed, thereby also improving the introduction of the larynx mask into the patient and adaptation of the position of the larynx mask to the anatomy and the position of the patient. Accordingly the guiding means 4 have two elements, namely a spring-back and/or adjustable pressure element 40 and a flexible traction element 41. The design of these two elements 40, 41 can vary greatly. The traction element 41 always comprises a flexible rope, wire or cable, which does not stretch at the forces occurring here and which can be mono- or multifilar. The materials used for this can also be very different, the only essential feature being that they are approved for medical purposes.

In a particularly simple form of embodiment as shown in FIG. 1, the pressure element 40 can be a relatively flat metal profile, square in cross-section, with relatively high elasticity, wherein this flat profile is designated 42 as a special example of embodiment of a pressure element. This flat profile 42 exhibits a bend which corresponds to the minimum bending of the supraglottic tube 1. The traction element 41 is attached directly or indirectly on the pressure element or on the flat profile 42 at its distal end. In the simplest case the traction element 41 can loosely project from the end of the supraglottic tube 1 and the surgeon could bring about bending by pulling on this traction element 41 with simultaneous counter-pressure on the tube at its proximal end or counter-pressure on the feed connector or the adjusting unit 3. For fixing in the end position the traction element 41 can be fixed at the required bending position to a corresponding fixing means, for example a simple hook. However, in the example shown here the fraction element 41 is firmly attached to a part of the feed connector and adjusting unit 3. This will be set out in below in the detailed description of the feed connector and adjusting unit 3.

Figure 2:
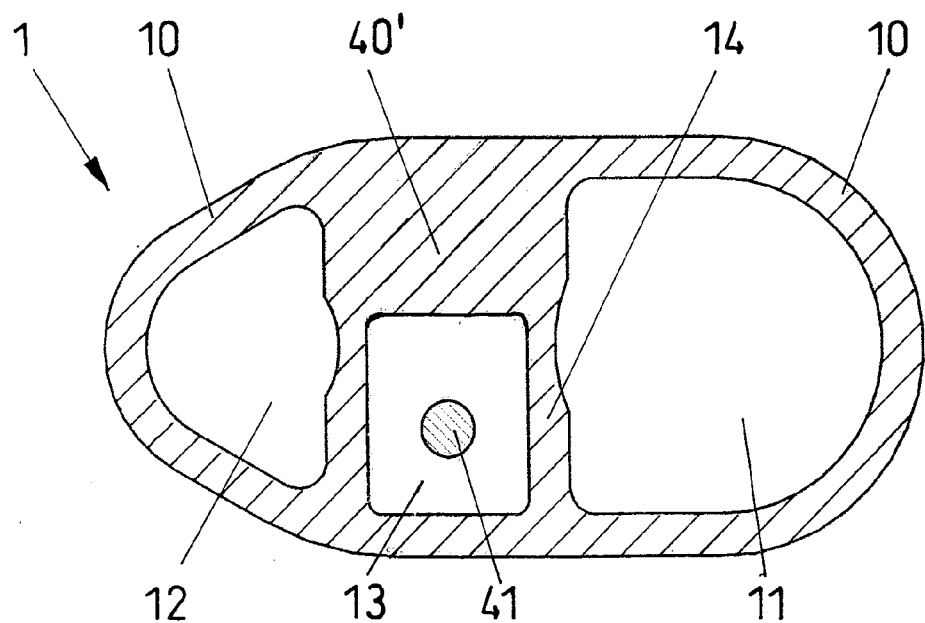
FIG. 2 shows an identical diametric section through a supraglottic tube with a dorsally reinforced wall area which forms the casing of a Bowden cable.

FIG. 2 shows a further form of embodiment of the guiding means 4. Whereas the traction element 41 is again in the form of a simple wire or cable, the pressure element is designated as 40' here and is an integral part of the supraglottic tube 1. The supraglottic tube 1 has a relatively thin outer wall 10 and the individual lumens 11, 12, 13 are separated from each other by separating walls 14.

In the embodiment in accordance with FIG. 2 the outer wall is strongly thickened in the area of the guiding lumen. In this way this outer wall area forms a pressure element 40'. Such an injection moulded or extruded supraglottic tube can be preformed with the minimum bend or can be produced as a straight part and then bent through pretensioning or after thermal treatment. The pressure element 40, 40', i.e. the thickened wall area or the flat profile 42, is always arranged on the dorsal side of the supraglottic tube, while the traction element lies on the ventral side of the supraglottic tube. As has already been stated, pulling on the traction element 41 leads to bending of the supraglottic tube 1; once this pulling ceases the supraglottic tube 1 returns to its original shape either through its own elasticity or with the aid of the elastic pressure element 40, 40'.

Figure 7:
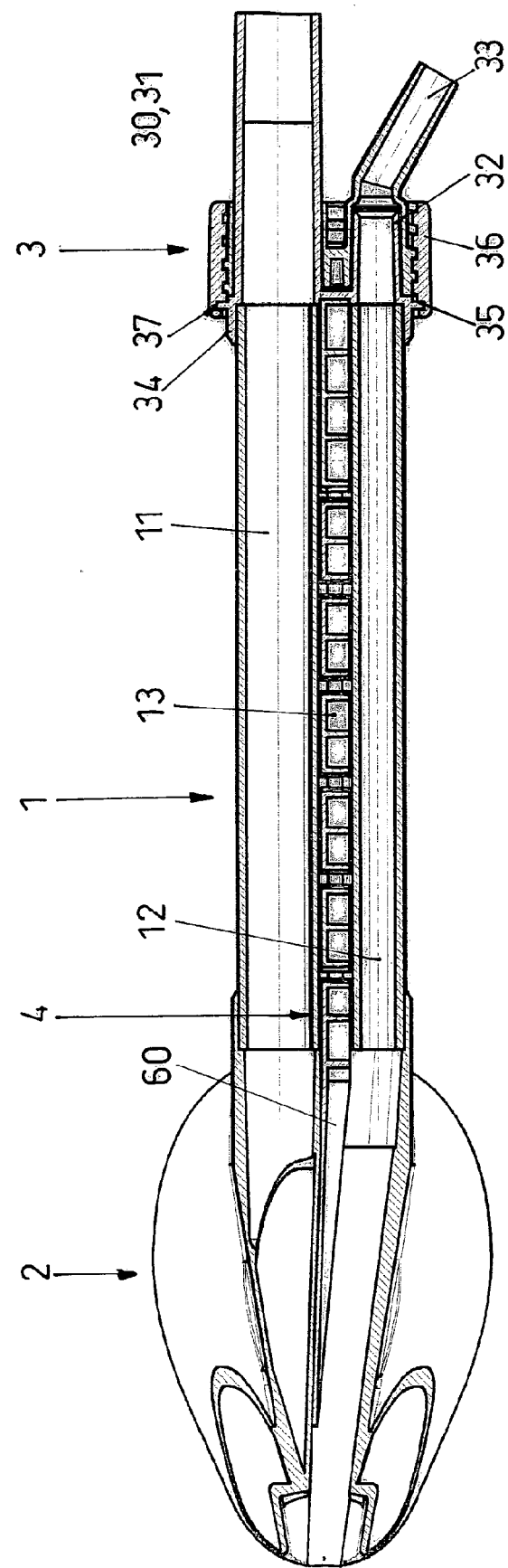
FIG. 7 shows a diametric longitudinal section through a supraglottic tube and the larynx mask with a supporting element.

A particularly preferred form of embodiment of the guiding element 4 is shown in FIGS. 3 and 7. Here the pressure element 40 is in the form of a preferably one-piece link chain 43. This link chain 43 has chain links 44 which can be of different sizes and are all connected via a dorsally continuous wall 45. Parallel to this dorsal wall 45 are two parallel ventral walls, namely an inner ventral wall 46 and an outer ventral wall 47. Both the inner ventral wall 46 and the outer ventral wall 47 have interruptions, or openings, 48' and 48" which are arranged so that they overlap. Between the inner ventral wall 46 and the outer ventral wall 47 there is an intermediate space 49 in which the traction element 41 is arranged. At the distal end of the link chain 43 there is an anchoring sleeve 50. This anchoring sleeve 50 is formed by a projection of the inner and outer ventral walls 46, 47. The fraction element 41 is here a monofilar string onto which a head 51 is formed. At the proximal end of the traction element 41 a cylindrical bearing head 52 is formed. The link chain 43 in the guiding lumen 13 also serves as compression/bite protection for the proximal supraglottic tube area.

In FIGS. 3 and 7 the combined feed connector and adjusting unit 3 is again seen in diametric section. The actual feed connector is designated as 30. Although it is in one piece, this feed connector 30 has two different connectors, namely the respiration air supply connector 31 and the oesophageal connector 32. The respiration air supply connector 31 is in communicating connection with the respiration lumen 11 and the oesophageal connector 32 is in communicating connection with the oesophageal lumen 12. The air supply connector 31 is straight and flush with the proximal end of the respiration lumen 11 or the supraglottic tube 1. The oesophageal connector 32 in the direct connection area to the oesophageal lumen 12 is also straight and flush therewith, but has a crimped, mounted end 33. In FIG. 3 only the air supply connector 31 is seen as in the shown position the oesophageal connector 32 is arranged directly behind it in the direction of view.

The combined feed connector 30 has a sealing sleeve 34 in which the supraglottic tube 1 is firmly held in sealed manner. As no large forces or high pressures occur in this area and the material of the supraglottic tube 1 is elastic, a pure frictional connection should suffice. However an adhesive connection may also be present or the sealing sleeve 34 can additionally be provided with one or more circumferential radial lips and corresponding circumferential radial grooves can be provided in the supraglottic tube 1 in order to thereby produce a form-fitted connection. A distally extended sealing sleeve 34 over the straight, proximal part of the supraglottic tube 1 also provides bite protection. Formed on the proximal end of the sealing sleeve 34 is a radially projecting sliding collar 35. This sliding collar 35 engages in a circumferential slide groove 37 which is formed in the distal end area of a union nut 36. In the union nut 36 is a traction pin 38, which is most clearly seen in FIG. 3. On rotation of the union nut 36 the fraction pin 38 only moves in the axial direction relative to the proximal end of the supraglottic tube 1. The traction pin 39 has a bearing cup 39 in which the cylindrical bearing head 52 is firmly held. As the traction pin 38 is only moved axially and does not rotate, the air supply connector 31 can easily pass through the traction pin 38. The oesophageal connector 32 also passes through the fraction pin 3 while the crimped end 33 is formed on the traction pin 38. A sliding seal therefore exists between the oesophageal connector 32 and the traction pin 38.

The supraglottic tube 1 in accordance with the invention can therefore be made of a relatively soft and flexible material which easily adapts to the anatomy. Due to the pressure element relatively high compressive strength comes about. In the inserted state, the guiding means 4 then allow the bending radius of the supraglottic tube 1 to be adjusted simply by turning the union nut 36. This stiffens the supraglottic tube and allows it to be introduced and positioned more easily due to its bent form. Secondarily, the bending radius of the supraglottic tube can be adapted to the anatomy or position of the patient so that the larynx mask 2 or its cuff 22 remain pressed around the larynx.

Once the supraglottic tube 1 has been inserted into the patient it is hardly noticeable whether the shape or the bending radius has already adjusted to the anatomy of the patient or not. Although at the minimum bending radius the respiration air supply connector 31 still projects from the traction pin 38, this is not evident to the eye. It is therefore proposed to apply a scale 28 (FIG. 3) to the respiration air supply connector in order to be able to read off the relative bending.

Figure 4:
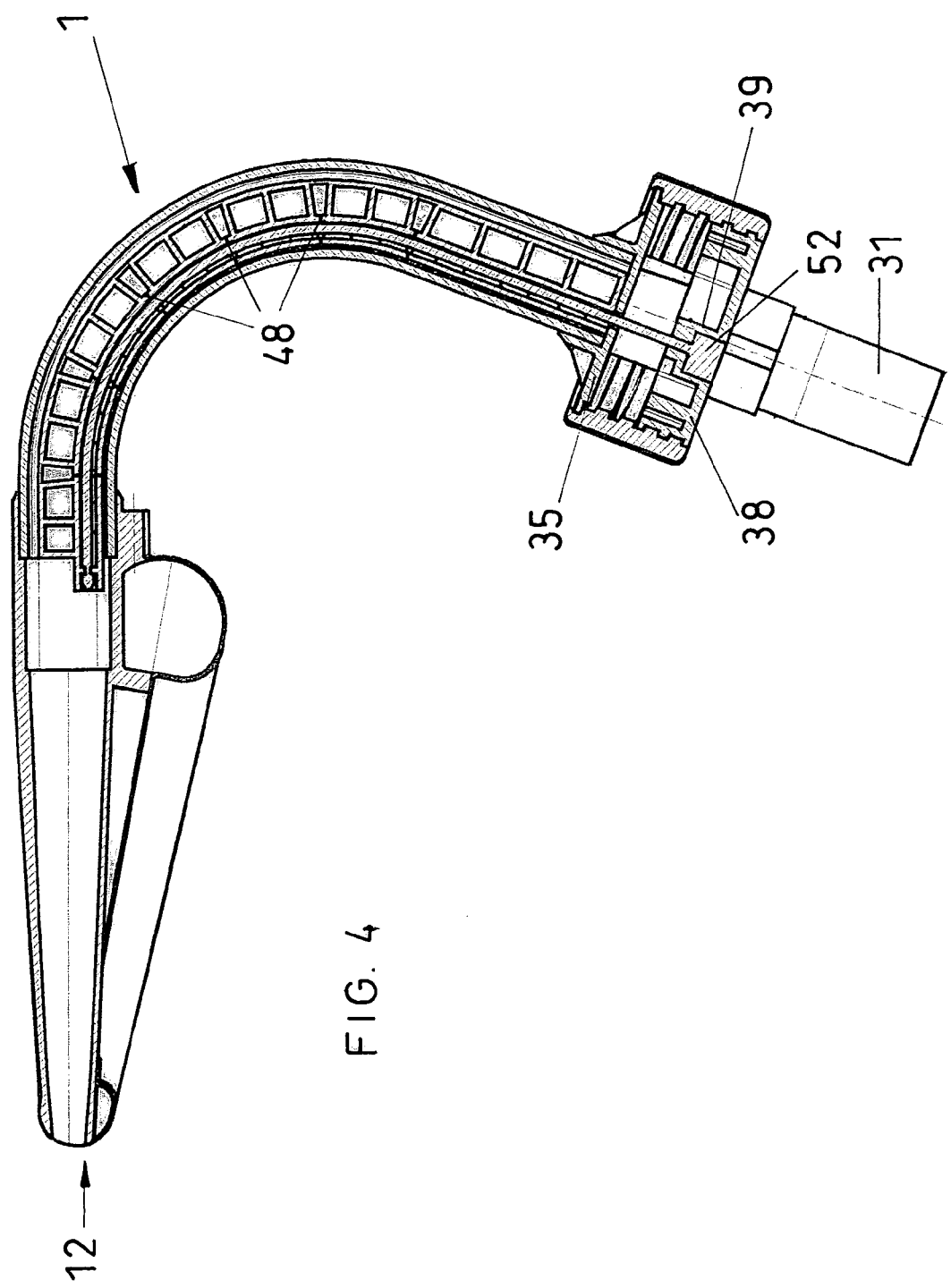
FIG. 4 shows the same arrangement as in FIG. 3, wherein the supraglottic tube is bent more strongly.

In FIG. 4 the supraglottic tube 1 together with the larynx mask 2 and the feed connector 3 is again shown in principle, but in a more curved state, whereby the traction pin 38 is accordingly moved in the proximal direction, whereby the section of the traction element 41 is pulled out further from the supraglottic tube 1 and thereby relatively shortened, while the length of the pressure element 40 remains unchanged.

Figure 5:
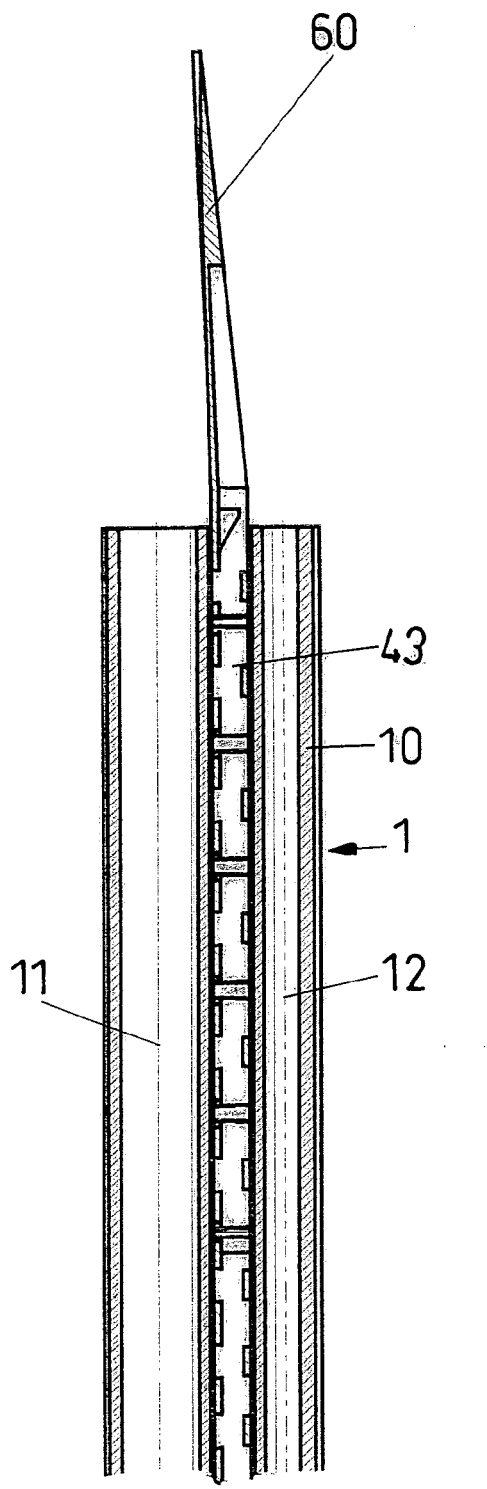
FIG. 5 shows the distal end of a supraglottic tube in a diametric section with a supporting element inserted into the larynx mask.
Figure 6:
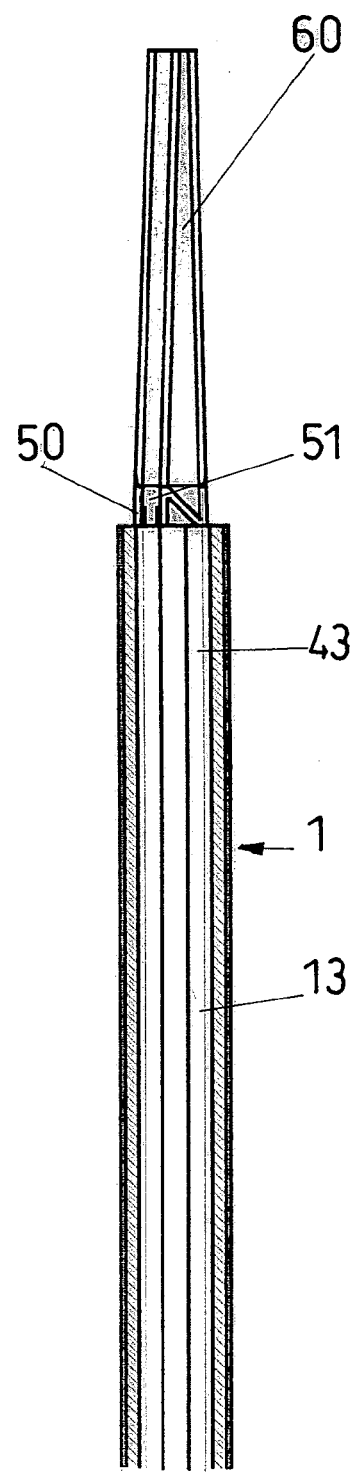
FIG. 6 shows a side view of the supraglottic tube with a similarly designed supporting element.

As, as has already been stated, the pressure that can absorbed by the supraglottic tube 1 is relatively high, it makes sense to also provide means that could serve to reinforce the larynx mask 2, in order, in particular, to largely prevent kinking of the larynx mask 2 in the area of the holding sleeve 21 of the larynx mask 2 itself and its tip 25. For this two solutions are shown schematically in FIGS. 5 and 6. FIGS. 5 and 6 show the supraglottic tube 1 in a view from above and from the side respectively, wherein only the distal end is shown schematically. In both cases a supporting element 60 is formed on the distal end of the link chain 43. In the view in accordance with FIG. 5 this supporting element 60 is designed as a vertical supporting wall. This supporting wall can be formed as an extension of the foremost, distal chain link. The height of the supporting wall 60 is reduced on both sides by the wall thickness of the outer wall 10 in order to facilitate introduction of the supporting element 60 into the larynx mask in the area of the holding sleeve 21. Naturally the larynx mask 2 must be designed accordingly so that the supporting well 60 can be introduced as far as possible into the area of the tip 25.

As, as shown in FIG. 5, the supporting wall runs practically perpendicularly to any possible bending of the larynx mask 2, the supporting force is correspondingly great and therefore this form of embodiment is preferred. While the supraglottic tube itself is made of a soft plastic, the pressure element 40, here in the form of a link chain 43, is made of hard plastic and is therefore extremely suitable as a supporting element 60. The entire guiding means 4 with the supporting wall or the supporting element 60 can be easily inserted into the supraglottic tube 1.

A particularly preferred form of embodiment of the guiding means 4 consists in the guiding means 4 being a fixed preformed element and can be introduced into the supraglottic tube or is fixed therein, whereby the element can be flexible=adaptable or not flexible.

A particularly preferred form of embodiment of the supraglottic tube contains, in an insertable or firmly fixed manner:
a. Inflation line for the cuff through the supraglottic tube
b. Thermosensor through the supraglottic tube
c. Respiration pressure measurement through the supraglottic tube
d. Respiratory gas measurement through the supraglottic tube
e. Optical image transmission through the supraglottic tube and
f. Measuring probe through the supraglottic tube.

An additional function of the guiding means consists in the fact that it can serve as bite protection.

LIST OF REFERENCE NUMBERS

1. Supraglottic tube
2. Larynx mask
3. Feed connector and adjusting unit
4. Guiding means
10. Outer wall
11. Respiration lumen
12. Oesophageal lumen
13. Guide lumen
14. Separating walls
20. Passage section of the larynx mask
21. Holding sleeve
22. Cuff or sealing collar
24. Internal chamber
25. Tip of the larynx mask
29. Scale for bending radius
30. Feed connector
31. Respiration air supply connector
32. Oesophageal connector
33. Crimped end of 32
34. Sealing sleeve
35. Sliding collar
36. Union nut
37. Circumferential sliding groove
38. Traction pin
39. Bearing cup
40, 40' Pressure element
41. Traction element
42. Flat profile
43. Link chain
44. Chain links
45. Dorsal wall of the link chain
46. Inner ventral wall
47. Outer ventral wall
48. Interruptions
49. Intermediate space
50. Anchoring sleeve
51. Head on traction element 41
52. Cylindrical bearing head
60. Supporting element

The invention claimed is:
1. A supraglottic tube for inserting a larynx mask via the pharynx comprising:
a respiration lumen that serves to supply respiration air and is used for instrumentation,
a guide lumen in which a guide element is positioned for changing a bending radius of the tube, wherein the guide element comprises: (a) a pressure element comprising (i) a link chain comprising chain links connected by a continuous dorsal wall and (ii) at least one ventral wall with openings therein; and (b) a flexible traction element, and
a supporting element formed on a distal end of the pressure element, wherein the supporting element extends to a distal tip of the larynx mask.

2. A supraglottic tube according to claim 1, further comprising an oesophageal lumen which serves as an oesophageal access.

3. A supraglottic tube according to claim 2 wherein the guide lumen is arranged medially between the two adjoining respiration and oesophageal lumens.

4. A supraglottic tube according to claim 1, wherein the guide lumen is closed at its distal end.

5. A supraglottic tube according to claim 1 wherein the supraglottic tube is provided in the form of a single tube and the respiration lumen and the guide lumen are formed by ventral-dorsally running separating walls.

6. A supraglottic tube according to claim 5 wherein at least one of the separating walls extends from a distal end of the tube and engages in the larynx mask as a ventral-dorsally running supporting element.

7. A supraglottic tube according to claim 6 wherein the supporting element extends distally to a tip of the larynx mask.

8. A supraglottic tube according to claim 1, wherein the flexible traction element is firmly anchored on a distal end of the pressure element.

9. A supraglottic tube according to claim 1 wherein a nut is attached at a proximal end of the supraglottic tube in which a traction pin, holding an end of the traction element is moveable relative to the proximal end of the supraglottic tube.

10. A supraglottic tube according to claim 1, wherein the pressure element comprises two parallel ventral walls with openings therein and wherein the traction element runs between the two parallel ventral walls.

11. A supraglottic tube according to claim 1, wherein the guide lumen has a rectangular cross-section and the chain links are rectangular.

12. A supraglottic tube for inserting a larynx mask via the pharynx, comprising:
a respiration lumen that supplies respiration air and is used for instrumentation,
an oesophageal lumen that serves as an oesophageal access,
a guide lumen positioned between the respiration lumen and the oesophageal lumen,
a guide element positioned in the guide lumen for changing a bending radius of the tube, wherein the guide element comprises: (a) a pressure element comprising (i) a one-piece link chain comprising chain links connected by a continuous dorsal wall and (ii) at least one ventral wall having openings therein; and (b) a flexible traction element, and
a supporting element formed on a distal end of the pressure element, wherein the supporting element extends into the larynx mask to its distal tip,
wherein the respiration lumen and the oesophageal lumen are separated by ventral-dorsally running separating walls, and wherein a separating wall between the guide lumen and the respiration lumen is arranged at least approximately in the center of the supraglottic tube.

13. A supraglottic tube according to claim 12, wherein the guide lumen is closed at its distal end.

14. A supraglottic tube according to claim 12, wherein the flexible traction element is firmly anchored on a distal end of the pressure element.

15. A supraglottic tube according to claim 12, wherein a nut is attached at a proximal end of the supraglottic tube in which a traction pin, holding an end of the traction element is moveable relative to the proximal end of the supraglottic tube.

16. A supraglottic tube according to claim 12, wherein the pressure element comprises two parallel ventral walls with openings therein and wherein the traction element runs between the two parallel ventral walls.

17. A supraglottic tube according to claim 12, wherein the guide lumen has a rectangular cross-section and the chain links are rectangular.

* * * * *